(12) United States Patent
Yamaguchi et al.

(10) Patent No.: US 7,834,193 B2
(45) Date of Patent: Nov. 16, 2010

(54) INDOLINE COMPOUND AND PROCESS FOR PRODUCING THE SAME

(75) Inventors: Toshiaki Yamaguchi, Nagano (JP); Ikuo Tsuchiya, Nagano (JP); Ken Kikuchi, Nagano (JP); Takashi Yanagi, Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 609 days.

(21) Appl. No.: 11/787,312

(22) Filed: Apr. 16, 2007

(65) Prior Publication Data

US 2007/0197627 A1 Aug. 23, 2007

Related U.S. Application Data

(63) Continuation of application No. PCT/JP2005/019478, filed on Oct. 24, 2005.

(51) Int. Cl.
*C07D 209/12* (2006.01)
*C07D 209/14* (2006.01)

(52) U.S. Cl. ..................................... 548/491
(58) Field of Classification Search ........................ None
See application file for complete search history.

(56) References Cited

U.S. PATENT DOCUMENTS 5,387,603 A    2/1995  Kitazawa et al.
6,310,086 B1 * 10/2001 Kitazawa et al. ............ 514/415

FOREIGN PATENT DOCUMENTS

| JP | 07-165684 |   | 6/1995 |
| JP | 2001-199956 |   | 7/2001 |
| JP | 2002-265444 | * | 9/2002 |
| JP | 2006-188470 | * | 7/2006 |

OTHER PUBLICATIONS

Greene et al. Protective Groups in Organic Synthesis, Chapter 2, "Protection for the Hydroxyl Group, Including 1,2- and 1,3-Dols," Third Edition, 1999, p. 17-21, 76-79 and 176.*
Kato et al., Machine translation of JP 2006-188470. Obtained on Aug. 5, 2010 from AIPN website. <http://dossier.ipdl.inpit.go.jp/text_trans.html>.*

* cited by examiner

*Primary Examiner*—Kamal A Saeed
*Assistant Examiner*—Alicia L Otton
(74) *Attorney, Agent, or Firm*—Frenkel & Associates, PC

(57) ABSTRACT

The present invention provides an industrial method production of silodosin, which is useful for a therapeutic agent for dysuria associated with benign prostatic hyperplasia. The production of silodosine is characterized by mixing 3-{7-cyano-5-[(2R)-2-({2-[2-(2,2,2-trifluoroethoxy)-phenoxy]ethyl}amino]propyl]-2,3-dihydro-1H-indol-1-yl}-propyl benzoate and oxalic acid to yield the oxalate, subsequently hydrolyzing the oxalate salt to yield 1-(3-hydroxypropyl)-5-[(2R)-2-({2-[2-(2,2,2-trifluoroethoxy)phenoxy]ethyl}amino]propyl]-2,3-dihydro-1H-indole-7-carbonitrile and hydrolyzing the same, and manufacturing intermediates used therefore.

10 Claims, No Drawings

INDOLINE COMPOUND AND PROCESS FOR PRODUCING THE SAME

CROSS-REFERNCE TO RELATED APPLICATIONS

This application is a continuation of Application No. PCT/JP2005/019478, filed Oct. 24, 2005. This application claims priority to PCT/JP2005/019478 and Japanese Application No. 313040/2004, filed Oct. 27, 2004.

TECHNICAL FIELD

The present invention relates to a method for production of an indoline compound useful as a medicine, and manufacturing intermediates therefor. More particularly, the present invention relates to a method for production of an indoline compound (general name: silodosin) represented by the following structural formula:

[Chem. 1]

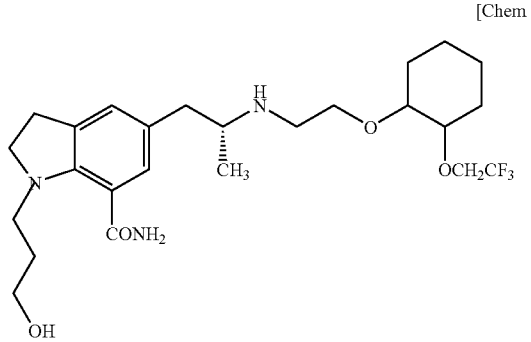

which is useful as a therapeutic agent for dysuria associated with benign prostatic hyperplasia, and manufacturing intermediates therefor for use in the production.

BACKGROUND ART

Silodosin has a selectively inhibitory effect against urethra smooth muscle constriction, and decreases urethra internal pressure without great influence on blood pressure. Furthermore, silodosin effects on an $\alpha_{1A}$-adrenoceptor subtype selectively, and is extremely useful as a therapeutic agent for dysuria associated with benign prostatic hyperplasia and the like (see Patent References 1 and 2).

As an effective and efficient method for production of silodosin, it is proposed or reported that an optically active amine compound represented by the following general formula:

[Chem. 2]

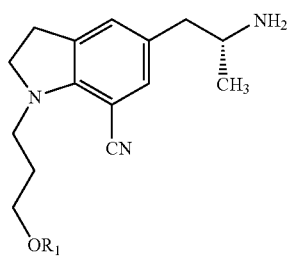

wherein $R^1$ represents a hydrogen atom or a hydroxyl-protective group, is allowed to react with a phenoxyethane compound represented by the following general formula:

[Chem. 3]

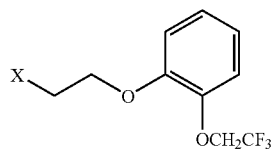

wherein X represents a leaving group, and optionally deprotected and the cyano group is converted to a carbamoyl group (see Patent References 3 and 4).

However, in the above-mentioned methods for production, a dialkyl compound (C) represented by the following general formula:

[Chem. 4]

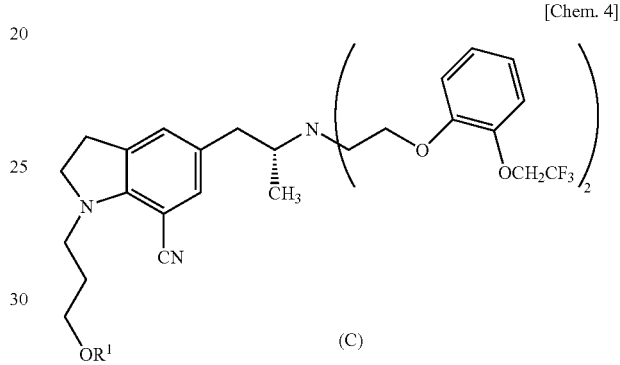

wherein $R^1$ represents a hydrogen atom or a hydroxyl-protective group, is sometimes generated as a by-product because of the reaction of one molecule of the optically active amine compound and two molecules of the phenoxyethane compound. Since it is difficult to remove the by-product by purification method used in a common industrial production such as recrystallization or the like, it is necessary to use purification method such as column chromatography or the like to remove the by-product. Therefore purification processes tend to be complex, are not satisfactory a method for industrial production. Thus, the development of a more applicable purification method for industrial production is required.

Patent Reference 1: Japanese Patent Publication H6-220015;
Patent Reference 2: Japanese Patent Publication 2000-247998;
Patent Reference 3: Japanese Patent Publication 2001-199956;
Patent Reference 4: Japanese Patent Publication 2002-265444.

DISCLOSURE OF THE INVENTION

Problem to Be Solved by the Invention

The object of the present invention is to provide a method for industrial production of silodosin.

Means of solving the Problems

To solve the above-mentioned object, the present inventors have studied earnestly and found that by converting 3-{7-cyano-5-[(2R)-2-({2-[2-(2,2,2-trifluoroethoxy)-phenoxy]

ethyl}amino)propyl]-2,3-dihydro-1H-indol-1-yl}-propyl benzoate represented by the following structural formula:

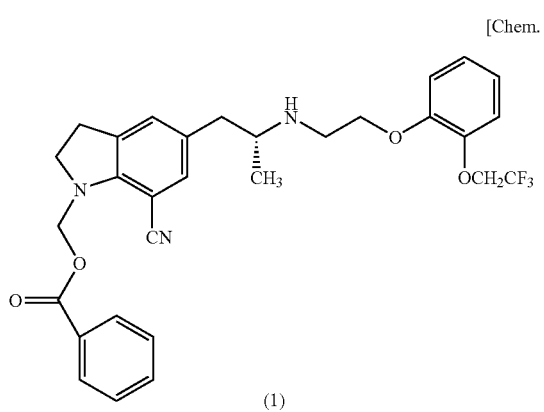

(1)

to the oxalate and isolating the same by crystallization, the by-product (C-a) represented by the formula:

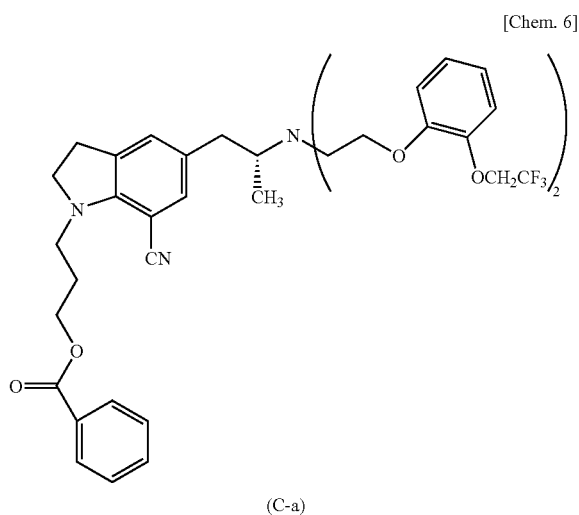

(C-a)

can be removed, thereby forming the bases of the present invention.

That is, the present invention relates to a method for production of 1-(3-hydroxypropyl)-5-[(2R)-2-({2-[2-(2,2,2-trifluoroethoxy)phenoxy]ethyl}amino)propyl]-2,3-dihydro-1H-indol-7-carboxamide represented by the structural formula (3):

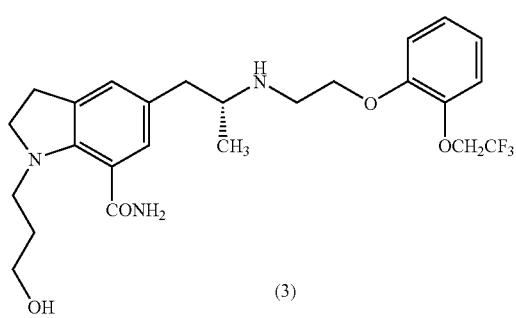

(3)

which comprises mixing 3-{7-cyano-5-[(2R)-2-({2-[2-(2,2,2-trifluoroethoxy)phenoxy]ethyl}amino)propyl]-2,3-dihydro-1H-indol-1-yl}propyl benzoate represented by the following formula (1):

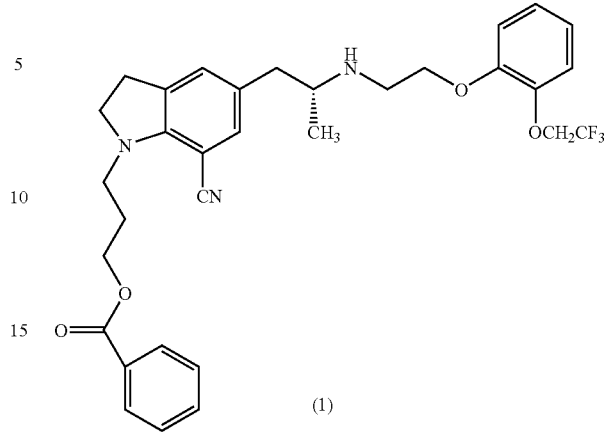

(1)

with oxalic acid to yield the 3-{7-cyano-5-[(2R)-2-({2-[2-(2,2,2-trifluoroethoxy)phenoxy]ethyl}amino)propyl]-2,3-dihydro-1H-indol-1-yl}propyl benzoate monooxalate, subsequently hydrolyzing the oxalate to yield 1-(3-hydroxypropyl)-5-[(2R)-2-({2-[2-(2,2,2-trifluoroethoxy)phenoxy]-ethyl}amino)propyl]-2,3-dihydro-1H-indole-7-carbonitrile represented by the structural formula(2):

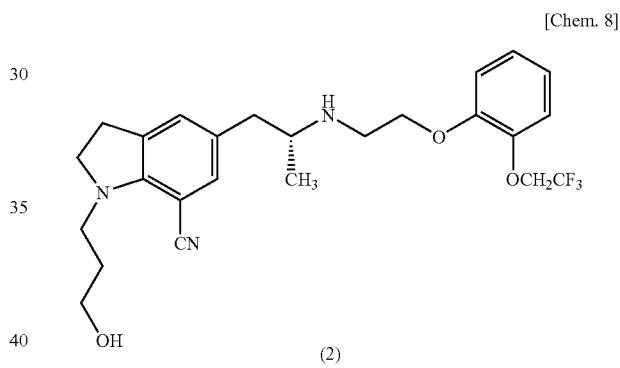

(2)

and further hydrolyzing the compound represented by the general formula (2), and manufacturing intermediates used in the method for production.

Effect of the Invention

3-{7-Cyano-5-[(2R)-2-({2-[2-(2,2,2-trifluoroethoxy)-phenoxy]ethyl}amino)propyl]-2,3-dihydro-1H-indol-1-yl}-propyl benzoate monooxalate generated as an intermediate in the method for production of the present invention crystallizes well, is easy to separate from the by-product (C-a) and easy to handle. Therefore, this oxalate becomes an extremely excellent intermediate in the method for industrial production.

BEST MODE TO PRACTICE THE INVENTION

The method for production of the present invention comprises 4 steps as explained below.

(Step 1)

Production of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate 3-{7-Cyano-5-[(2R)-2-({2-[2-(2,2,2-trifluoroethoxy)-phenoxy]ethyl}amino)propyl]-2,3-dihydro-1H-indol-1-yl}- propyl benzoate used in the method for production of the present invention can be prepared in a similar method as described in Patent Reference 3, by allowing 3-{7-cyano-5-[(2R)-2-aminopropyl]-2,3-dihydro-1H-indol-1-yl}propyl benzoate represented by the structural formula(A):

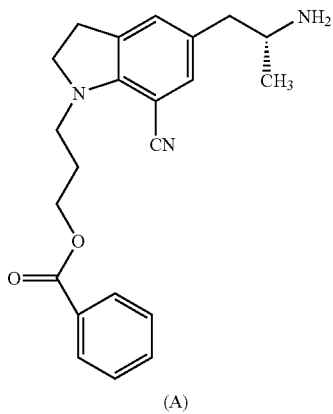

(A)

or a salt thereof to react with a phenoxyethane compound represented by the general formula(B):

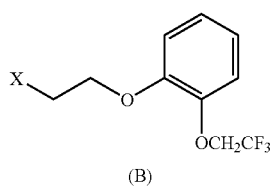

(B)

wherein X represents a leaving group,
in an organic solvent and preferably in the presence of a base.

As the leaving group X of the general formula (B), for example, a chlorine atom, a bromine atom and an iodine atom, a lower alkyl sulfonyloxy group such as a methanesulfonyloxy group and the like, an arylsulfonyloxy group such as a benzenesulfonyloxy group or a toluenesulfonyloxy group and the like can be illustrated. Among them, the lower alkylsulfonyloxy group is preferable.

As the organic solvent used in the reaction solvent, any organic solvent can be usable unless it inhibits the reaction. For example, a lower alcohol such as methanol, ethanol, propanol, isopropyl alcohol, tert-butanol and the like; an aprotic polar solvent such as dimethylformamide, dimethylsulfoxide, acetonitrile and the like, and a mixture of solvents selected from the same can be illustrated. Among them, the lower alcohol is preferable, especially tert-butanol. is the most preferable.

As the base, for example, an inorganic base such as an alkali metal hydroxide such as sodium hydroxide, potassium hydroxide and the like, an alkali metal carbonate salt such as sodium carbonate, potassium carbonate, cesium carbonate and the like, and an organic base such as a lower alkyl amine such as triethylamine, diisopropylamine and the like can be illustrated. Among them, an inorganic base, especially an alkali metal carbonate is preferable, and sodium carbonate is especially preferable.

The reaction may be usually performed at from room temperature to a boiling point of an organic solvent used for the reaction for 30 minutes to 48 hours.

After the reaction, 3-{7-cyano-5-[(2R)-2-({2-[2-(2,2,2-trifluoroethoxy)phenoxy]ethyl}amino)propyl-2,3-dihydro-1H-indol-1-yl}propyl benzoate can be obtained by a usual procedure. The above-mentioned by-product (C-a) is included in the product around 5 to 20% usually, though it is different depending on the reaction condition. The amount of the by-product contained can be calculated by a ratio of area measured by high performance liquid chromatography in the following conditions.

Measuring Conditions
Column: Inertsil ODS-2
Wave length: 254 nm
Mobile phase: Methanol: 0.01 mol/L phosphate buffer (pH 7.6)=17:3

(Step 2)

Production of 3-{7-cyano-5-[(2R)-2-({2-[2-(2,2,2-trifluoroethoxy)phenoxy]ethyl}amino]propyl]-2,3-dihydro-1H-indol-1-yl}propyl benzoate monooxalate.

A crystal of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate monooxalate can be isolated by dissolving almost equimolar amounts of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate and oxalic acid in a suitable solvent and optionally heating the solution to form 3-{7-cyano-5-[(2R)-2-({2-[2-(2,2,2-trifluoroethoxy)-phenoxy]ethyl}amino)propyl]-2,3-dihydro-1H-indol-1-yl}-propyl benzoate monooxalate and crystallizing out the same. As the solvent, for example, a lower alcohol such as methanol, ethanol, propanol, isopropyl alcohol and the like or the above lower alcohol containing water, a mixture of solvents selected from the same and the like can be illustrated. Among them, a lower alcohol is preferable, especially ethanol, isopropyl alcohol and a mixed solvent of water and isopropyl alcohol is preferable.

Though it can be depending on the solvent, a preferable amount of oxalic acid to be used is from usually 0.7 to 1.5 equivalents to 3-{7-cyano-5-[(2R)-2-({2-[2-(2,2,2-trifluoroethoxy)phenoxy]ethyl}amino)propyl]72,3-dihydro-1H-indol-1-yl}propyl benzoate.

A crystal of the oxalate can be crystallized out by leaving the above oxalate solution. At this time, optionally seeding crystals of the oxalate or cooling down may be used. Furthermore, the oxalate can be also crystallized out by concentrating the oxalate solution or dropping a poor solvent into the oxalate solution.

The amount of by-product (C-a) contained can be reduced 1% or less by the above-mentioned method, by way of 3-{7-cyano-5-[(2R)-2-({2-[2-(2,2,2-trifluoroethoxy)-phenoxy]ethyl}amino)propyl]-2,3-dihydro-1H-indol-1-yl}-propyl benzoate monooxalate. Therefore, an obtained oxalate can be used in the next reaction directly.

(Step 3)

Production of 1-(3-hydroxypropyl)-5-[(2R)-2-({2-[2-(2,2,2-trifluoroethoxy)phenoxy]ethyl}amino)propyl]-2,3-dihydro-1H-indole-7-carbonitrile 1-(3-Hydroxypropyl)-5-[(2R)-2-({2-[2-(2,2,2-trifluoroethoxy)phenoxy]ethyl}amino)propyl]-2,3-dihydro-1H-indole-7-carbonitrile can be prepared by hydrolyzing 3-{7-cyano-5-[(2R)-2-({2-[2-(2-,2,2-trifluoroethoxy)-phenoxy]ethyl}amino)propyl]-2,3-dihydro-1H-indol-1-yl}-propyl benzoate monooxalate in a suitable solvent.

The hydrolysis reaction can be performed using an alkali such as an alkali metal hydroxide such as sodium hydroxide, potassium hydroxide or the like; an alkali metal carbonate salt such as sodium carbonate, potassium carbonate, cesium carbonate or the like, or using an acid such as hydrochloric acid, hydrobromic acid, sulfuric acid, nitric acid or the like. Among them, an alkali is preferable, especially an alkali metal hydroxide is preferable.

As the solvent used in hydrolysis, water; a lower alcohol such as methanol, ethanol, propanol, isopropyl alcohol and the like; a water soluble organic solvent such as acetone, tetrahydrofuran, dioxane and the like, and a mixture of solvents selected from the same can be illustrated. Among them, a mixed solvent of water and a lower alcohol is preferable.

The hydrolysis reaction may be performed usually at from 0° C. to a boiling point of an used solvent for 30 minutes to 48 hours, and then 1-(3-hydroxypropyl)-5-[(2R)-2-({2-[2-(2,2,2-trifluoroethoxy)phenoxy]ethyl}amino)propyl]-2,3-dihydro-1H-indole-7-carbonitrile can be obtained by a usual procedure. The obtained compound may be used in the next reaction directly or optionally after further purification.

(Step 4)
Production of 1-(3-hydroxypropyl)-5-[(2R)-2-({2-[2-(2,2,2-trifluoroethoxy)phenoxy]ethyl}amino)propyl]-2,3-dihydro-1H-indole-7-carboxamide 1-(3-Hydroxypropyl)-5-[(2R)-2-({2-[2-(2,2,2-trifluoroethoxy)phenoxy]ethyl}amino)propyl]-2,3-dihydro-1H-indole-7-carboxamide can be prepared by hydrolyzing 1-(3-hydroxypropyl)-5-[(2R)-2-({2-[2-(2,2,2-trifluoroethoxy)phenoxy]ethyl}amino)propyl]-2,3-dihydro-1H-indole-7-carbonitrile in a suitable solvent.

The hydrolysis reaction can be performed using an alkali such as an alkali metal hydroxide such as sodium hydroxide, potassium hydroxide or the like; alkali metal carbonate such as sodium carbonate, potassium carbonate, cesium carbonate or the like, or using an acid such as hydrochloric acid, hydrobromic acid, sulfuric acid, nitric acid or the like. Among them, an alkali is preferable, especially an alkali metal hydroxide is preferable. In addition, it is preferable that the hydrolysis reaction is performed in the presence of an oxidizing agent such as hydrogen peroxide or the like.

As the solvent used in hydrolysis, water; a lower alcohol such as methanol, ethanol, propanol, isopropyl alcohol and the like; a water soluble organic solvent such as acetone, tetrahydrofuran, dioxan, dimethylsulfoxide and the like; and a mixture of solvents selected from the same and the like can be illustrated. Among them, a mixed solvent of water and dimethylsulfoxide is preferable.

The hydrolysis reaction may be performed at from 0° C. to 100° C. for 30 minutes to 48 hours, and then 1-(3-hydroxypropyl)-5-[(2R)-2-({2-[2-(2,2,2-trifluoroethoxy)phenoxy]ethyl}-amino)propyl]-2,3-dihydro-1H-indole-7-carboxamide can be obtained by a usual procedure.

EXAMPLES

The present invention is further illustrated in more detail by way of the following Examples, however the invention is not limited thereto.

Example 1

3-{7-cyano-5-[(2R)-2-({2-[2-(2,2,2-trifluoroethoxy)-phenoxy]ethyl}amino)propyl)-2,3-dihydro-1H-indol-1-yl)-propyl benzoate To a mixture of ethyl acetate (50 mL) and an aqueous solution (50 mL) of potassium carbonate (13.5 g), 3-[5-((2R)-2-aminopropyl)-7-cyano-2,3-dihydro-1H-indol-1-yl]propyl benzoate (2R,3R)-monotartarate (5.0 g) was added little by little, and the mixture was stirred at room temperature for 2 hours. The ethyl acetate layer was separated, and the aqueous layer was extracted with an ethyl acetate solution (50 mL). The combined ethyl acetate layer was washed with an aqueous potassium carbonate solution and dried over anhydrous sodium sulfate. The filtrate was concentrated under reduced pressure. The obtained oil was dissolved in anhydrous tert-butanol (25 mL), and to the solution were added 2-[2-(2,2,2-trifluoroethoxy)phenoxy]ethyl methanesulfonate (3.67 g) and sodium carbonate (1.08 g). The mixture was refluxed by heating for 24 hours. After the reaction mixture was allowed to cool and then added an aqueous sodium bicarbonate solution (50 mL). The mixture was extracted twice with ethyl acetate (50 mL). The combined ethyl acetate layer was washed with an aqueous sodium bicarbonate solution, water and brine and dried over anhydrous sodium sulfate. The filtrate was concentrated under reduced pressure to give 3-{7-cyano-5-[(2R)-2-({2-[2-(2,2,2-trifluoroethoxy)phenoxy]ethyl}amino)propyl]-2,3-dihydro-1H-indol-1-yl}propyl benzoate (6.40 g). At this time, the content of by-product (C-a) in the obtained product was 13.6%. The product was used in the next reaction. The obtained structure of 3-{7-cyano-5-[(2R)-2-({2-[2-(2,2,2-trifluoroethoxy)-phenoxy]ethyl}amino)propyl]-2,3-dihydro-1H-indol-1-yl}-propyl benzoate was confirmed by NMR analysis using a purified part of the product.

$^1$H-NMR (CDCl$_3$) δppm: 1.06 (3H, d, J=6.4 Hz), 2.15 (2H, m), 2.44 (1H, dd, J=6.9, 13.8 Hz), 2.61 (1H, dd, J=6.3, 13.8 Hz), 2.85-3.10 (5H, m), 3.57 (2H, t, J=8.6 Hz), 3.74 (2H, t, J=7.2 Hz), 4.05-4.15 (2H, m), 4.32 (2H, q, J=8.4 Hz), 4.47 (2H, t, J=6.4 Hz), 6.89-7.06 (6H, m), 7.44 (2H, t, J=7.8 Hz), 7.55 (1H, t, J=7.5 Hz), 8.06 (2H, d, J=8.4 Hz).

Example 2

3-{7-cyano-5-[(2R)-2-({2-[2-(2,2,2-trifluoroethoxy)-phenoxy]ethyl}amino)propyl]-2,3-dihydro-1H-indol-1-yl}-propyl benzoate monooxalate Isopropyl alcohol (50 mL) and oxalic acid dihydrate (1.20 g) were added to 3-{7-cyano-5-[(2R)-2-({2-[2-(2,2,2-trifluoroethoxy)phenoxy]ethyl}amino)propyl]-2,3-dihydro-1H-indol-1-yl}propyl benzoate (6.40 g) which was obtained in the Example 1, and the mixture was dissolved by heating. After seeding of the title compound, the mixture was stood overnight. The precipitated crystals were collected by filtration and washed with a small amount of cooled isopropyl alcohol and dried under vacuum to give 3-{7-cyano-5-[(2R)-2-({2-[2-(2,2,2-trifluoroethoxy)phenoxy]ethyl}amino)propyl]-2,3-dihydro-1H-indol-1-yl}propyl benzoate mono oxalate (5.43 g). At this time, the content of by-product (C-a) in the obtained product was 0.9%.

$^1$H-NMR (DMSO-d$_6$) δppm: 1.13 (3H, d, J=6.2 Hz), 2.08 (2H, m), 2.45-2.57 (1H, m), 2.88-3.05 (3H, m), 3.35-3.50 (3H, m), 3.60 (1H, t, J=8.6 Hz), 3.70 (2H, t, J=7.1 Hz), 4.29 (2H, brs), 4.39 (2H, t, J=6.1 Hz), 4.71 (2H, q, J=8.9 Hz), 6.95-7.16 (6H, m), 7.51 (2H, t, J=7.7 Hz), 7.65 (1H, t, J=7.4 Hz), 7.99 (2H, d, J=7.4 Hz).

Example 3

1-(3-hydroxypropyl)-5-[(2R)-2-({2-[2-(2,2,2-trifluoroethoxy)phenoxy]ethyl}amino)propyl]-2,3-dihydro-1H-indole-7-carbonitrile 3-{7-Cyano-5-[(2R)-2-({2-[2-(2,2,2-trifluoroethoxy)-phenoxy]ethyl}amino)propyl]-2,3-dihydro-1H-indol-1-yl}-propyl benzoate monooxalate(10.0 g) was dissolved. in methanol (40 mL), then an aqueous potassium hydroxide solution, which was prepared from potassium hydroxide (2.93 g) and water (10 mL) was added little by little, and the mixture was stirred at room temperature for overnight. To the reaction mixture, water (150 mL) was added and extracted with ethyl acetate (150 mL and 50 mL) successively. The combined ethyl acetate layer was washed with a saturated aqueous sodium bicarbonate solution and brine and dried over anhydrous sodium sulfate. The filtrate was concentrated under reduced pressure to give 1-(3-hydroxypropyl)-5-[(2R)-2-({2-[2-(2,2,2-trifluoroethoxy)phenoxy]-ethyl}amino)propyl]-2,3-dihydro-1H-indole-7-carbonitrile (7.86 g).

$^1$H-NMR (CDCl$_3$) δppm: 1.05 (3H, d, J=6.1 Hz), 1.85-1.95 (2H, m), 2.43 (1H, dd, J=13.5, 6.8 Hz), 2.60 (1H, dd, J=13.7, 6.3 Hz), 2.80-3.10 (5H, m), 3.57 (2H, t, J=8.8 Hz), 3.67 (2H, t, J=7.2 Hz), 3.80 (2H, t, J=6.0 Hz), 4.05-4.15 (2H, m), 4.32 (2H, q, J=8.4 Hz), 6.85-7.05 (5H, m).

Example 4

1-(3-Hydroxypropyl)-5-[(2R)-2-({2-[2-(2,2,2-trifluoroethoxy)phenoxy]ethyl}amino)propyl]-2,3-dihydro-1H-indole-7-carboxamide 1-(3-Hydroxypropyl)-5-[(2R)-2-({2-[2-(2,2,2-trifluoroethoxy)phenoxy]ethyl}amino)propyl]-2,3-dihydro-1H-indole-7-carbonitrile(6.00 g) was dissolved in dimethylsulfoxide (75 mL), and to the solution was added 5 mol/L aqueous sodium hydroxide solution(4.50 mL). To the reaction mixture, 30% hydrogen peroxide (2.63 mL) was added little by little at not more than 25° C. The reaction mixture was stirred at 20 to 25° C. for 5 hours. To the reaction mixture, an aqueous sodium sulfite solution of sodium sulfite (2.1 g) dissolved in water (150 mL) was added carefully. The reaction mixture was extracted twice with ethyl acetate (50 mL). The combined ethyl acetate layer was extracted twice with 2 mol/L hydrochloric acid. The aqueous hydrochloric acid solution extracted was neutralized with sodium bicarbonate, and extracted twice with ethyl acetate (50 mL). The combined ethyl acetate layer was washed with a saturated aqueous sodium bicarbonate solution and brine and dried over anhydrous sodium sulfate. The filtrate was concentrated under reduced pressure, and the residue was dissolved in ethyl acetate. The solution was cooled to give 1-(3-hydroxypropyl)-5-[(2R)-2-({2-[2-(2,2,2-trifluoroethoxy)phenoxy]-ethyl}amino)propyl]-2,3-dihydro-1H-indole-7-carboxamide (4.49 g).

$^1$H-NMR (CDCl$_3$) δppm: 1.08 (3H, d, J=6.2 Hz), 1.75-1.85 (2H, m), 2.53 (1H, dd, J=13.6, 6.7 Hz), 2.68 (1H, dd, J=13.6, 6.6 Hz), 2.90-3.10 (5H, m), 3.19 (2H, t, J=6.7 Hz), 3.41 (2H, t, J=8.5 Hz), 3.75 (2H, t, J=5.6 Hz), 4.05-4.15 (2H, m), 4.30 (2H, q, J=8.4), 5.79 (1H, bs), 6.65 (1H, bs), 6.85-7.05 (5H, m), 7.16 (1H, s).

The invention claimed is:

1. A method for production of 1-(3-hydroxypropyl)-5-[(2R)-2-({2-[2-(2,2,2-trifluoroethoxy)phenoxy]ethyl}amino)-propyl]-2,3-dihydro-1H-indole-7-carboxamide of the structural formula (3):

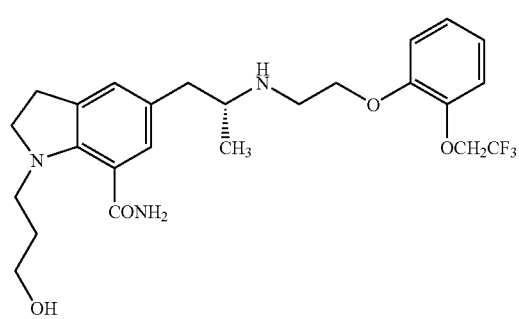

(3)

comprising mixing 3-{7-cyano-5-[(2R)-2-({2-[2-(2,2,2-trifluoroethoxy)phenoxy]-ethyl}amino)propyl]2,3-dihydro-1H-indol-1-yl}propyl benzoate of the structural formula (1):

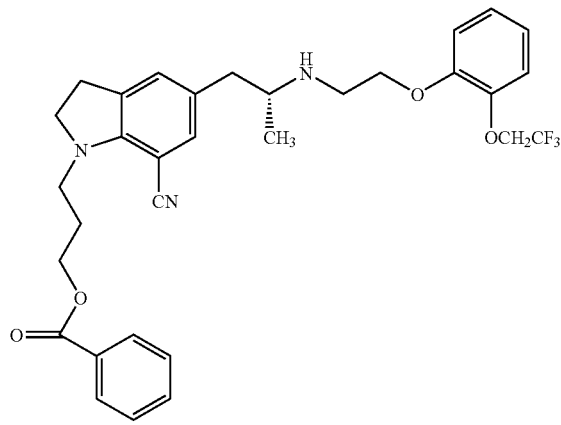

(1)

with oxalic acid to yield 3-{7-cyano-5-[(2R)-2-({2-[2-(2,2,2-trifluoroethoxy)phenoxy]-ethyl)amino)propyl]-2,3-dihydro-1H-indol-1-yl)propyl benzoate monooxalate, subsequently hydrolyzing the oxalate to yield 1-(3-hydroxypropyl)-5-[(2R)-2-({2-[2-(2,2,2-trifluoroethoxy)phenoxy]ethyl}amino)propyl]-2,3-dihydro-1H-indole-7-carbonitrile of the structural formula (2):

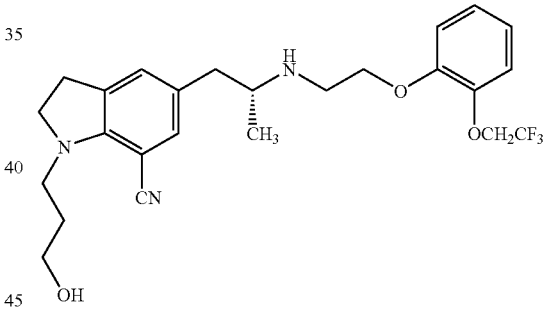

(2)

and hydrolyzing the compound of the structural formula (2).

2. A method for production as claimed in claim 1, which comprises isolating 3-{7-cyano-5-[(2R)-2-({2-[2-(2,2,2-trifluoroethoxy)phenoxy]ethyl)amino)propyl]-2,3-dihydro-1H-indol-1-yl)propyl benzoate monooxalate.

3. A method for production as claimed in claim 1, which comprises hydrolyzing 3-{7-cyano-5-[(2R)-2-({2-[2-(2,2,2-trifluoroethoxy)phenoxy]ethyl)amino)propyl]-2,3-dihydro-1H-indol-1-yl)propyl benzoate monooxalate with an alkali metal hydroxide.

4. A method for production as claimed in any one of claims 1 to 3, wherein 1-(3-hydroxypropyl)-5-[(2R)-2-({2-[2-(2,2,2-trifluoroethoxy)phenoxy]ethyl)amino)propyl]-2,3-dihydro-1H-indole-7-carbonitrile is hydrolyzed in the presence of an oxidizing agent.

5. A method for production as claimed in claim 4, wherein the oxidizing agent is hydrogen peroxide.

6. A method for production of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate monooxalate, which comprises mixing 3-{7-cyano-5-[(2R)-2-({2-[2-(2,2,2-trifluoroethoxy)phenoxy]ethyl}amino)propyl]-2,3-dihydro-1H-indol1-yl}propyl benzoate and oxalic acid.

7. A method for production of 1-(3-hydroxypropyl)-5-[(2R)-2-({2-[2-(2,2,2-trifluoroethoxy)phenoxy] ethyl}amino)-propyl]2,3-dihydro-1H-indole-7-carbonitrile of the structural formula (2):

(2)
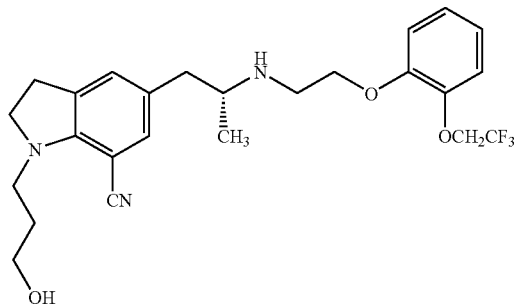

which comprises hydrolyzing 3-{7-cyano-5-[(2R)-2-({2-[2-(2,2,2-trifluoroethoxy)-phenoxy]ethyl}amino)propyl]-2,3-dihydro-1H-indol-1-yl}propyl benzoate monooxalate.

8. A method for production of 1-(3-hydroxypropyl)-5-[(2R)-2-({2-[2-(2,2,2-trifluoroethoxy)phenoxy] ethyl}amino)propyl]-2,3-dihydro-1H-indole-7-carboxamide of the structural formula (3):

(3)
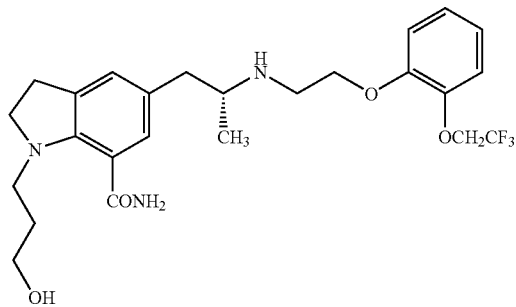

which comprises hydrolyzing 1-(3-hydroxypropyl)-5-[(2R)-2-({2-[2-(2,2,2-trifluoroethoxy)phenoxy]ethyl}amino)propyl]-2,3-dihydro-1H-indole-7-carbonitrile, wherein said 1-(3-hydroxypropyl)-5-[(2R)-2-({2-[2-(2,2,2-trifluoroethoxy)phenoxy]-ethyl}amino)propyl]-2,3-dihydro-1H-indole-7-carbonitrile is produced according to the method of claim 7.

9. 3-{7-Cyano-5-[(2R)-2-({2-[2-(2,2,2-trifluoroethoxy)phenoxy]ethyl}amino)propyl]-2,3-dihydro-1H-indol-1-yl}propyl benzoate monooxalate.

10. A method for production as claimed in claim 6, wherein said 3-{7-cyano-5-[(2R)-2-({2-[2-(2,2,2-trifluoroethoxy)phenoxy]ethyl}amino)propyl]-2,3-dihydro-1H-indol-1-yl}propyl benzoate is produced by allowing 3-{7-cyano-5-[(2R)-2-aminopropyl-2,3-dihydro-1H-indol-1-yl)propyl benzoate of the structural formula (A):

(A)
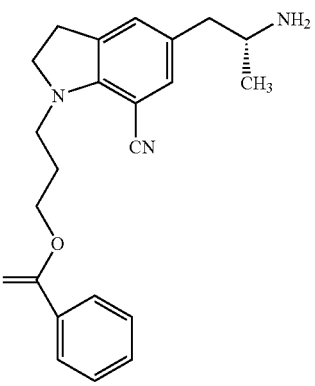

to react with a phenoxyethane compound of the formula (B):

(B)
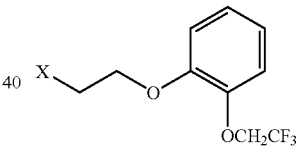

wherein X represents a leaving group.

* * * * *